United States Patent
Nishimura et al.

(10) Patent No.: US 9,700,625 B2
(45) Date of Patent: Jul. 11, 2017

(54) LIQUID ANTISEPTIC COMPOSITION AND METHOD FOR PRODUCING THE SAME

(71) Applicant: UENO FINE CHEMICALS INDUSTRY, LTD., Osaka-shi, Osaka (JP)

(72) Inventors: Munehiro Nishimura, Takarazuka (JP); Hiroki Tsunematsu, Osaka (JP); Toshihide Komatsu, Kobe (JP)

(73) Assignee: UENO FINE CHEMICALS INDUSTRY, LTD., Osaka (JP)

( * ) Notice: Subject to any disclaimer, the term of this patent is extended or adjusted under 35 U.S.C. 154(b) by 0 days.

(21) Appl. No.: 15/131,462

(22) Filed: Apr. 18, 2016

(65) Prior Publication Data

US 2016/0317663 A1    Nov. 3, 2016

(30) Foreign Application Priority Data

Apr. 30, 2015   (JP) .................................. 2015-093006

(51) Int. Cl.
    *A61K 47/10*    (2017.01)
    *A61K 31/235*   (2006.01)
    *A01N 37/40*    (2006.01)

(52) U.S. Cl.
    CPC ............... *A61K 47/10* (2013.01); *A01N 37/40* (2013.01); *A61K 31/235* (2013.01)

(58) Field of Classification Search
    CPC .............................. A61K 47/10; A61K 31/235
    USPC ........................................................ 514/544
    See application file for complete search history.

(56) References Cited

U.S. PATENT DOCUMENTS 5,641,808 A    6/1997   Gaffney et al.

FOREIGN PATENT DOCUMENTS

| CN | 104222080 A | 12/2014 | |
|----|-------------|---------|---|
| DE | EP 0194466 A2 * | 9/1986 | ............. A01N 37/40 |
| EP | 0194466 A2 | 9/1986 | |
| JP | 37-17994 B | 11/1962 | |
| JP | 9-124414 A | 5/1997 | |
| JP | 2003-252799 A | 9/2003 | |

OTHER PUBLICATIONS

Giordano, F et al. "Physical Properties of Parabens and Their Mixtures: Solubility in Water, Thermal Behavior, and Crystal Structures", Journal of Pharmaceutical Sciences, American Pharmaceutical Association, Washington, US, vol. 88, No. 11, Nov. 1, 1999, pp. 1210-1216.

Communication dated Jun. 16, 2016 from the European Patent Office issued in corresponding Application No. 16165963.6.

\* cited by examiner

*Primary Examiner* — Yong Chu
(74) *Attorney, Agent, or Firm* — Sughrue Mion, PLLC

(57) ABSTRACT

The present invention provides a liquid antiseptic composition including (A) parahydroxybenzoic acid ester and (B) water-miscible organic solvent, wherein the (A) parahydroxybenzoic acid ester are two or more esters selected from the group consisting of methyl parahydroxybenzoate, ethyl parahydroxybenzoate, propyl parahydroxybenzoate, isopropyl parahydroxybenzoate, butyl parahydroxybenzoate, isobutyl parahydroxybenzoate and benzyl parahydroxybenzoate; the (B) water-miscible organic solvent contains (B-1) at least one organic solvent selected from the group consisting of propylene glycol, butylene glycol, ethanol and polyethylene glycol, and (B-2) 2-phenoxyethanol; and a weight ratio of (A) and (B) is 1:1 to 1:3, and a weight ratio of (B-1) and (B-2) is 1:1 to 1:3.

9 Claims, No Drawings

LIQUID ANTISEPTIC COMPOSITION AND METHOD FOR PRODUCING THE SAME

BACKGROUND OF THE INVENTION

1. Field of the Invention

The present invention claims the priority under the Paris Convention based on Japanese Patent Application No. 2015-093006 (filing date: Apr. 30, 2015), the entirety of which is hereby incorporated herein by reference.

The present invention relates to a liquid antiseptic composition containing parahydroxybenzoic acid ester.

2. Description of the Related Art

Parahydroxybenzoic acid ester has excellent antibacterial activity, low toxicity, and low irritation, so that various esters are used as an antiseptic for cosmetics or the like. However, parahydroxybenzoic acid ester has extremely low solubility in water, and thus may be precipitated as crystals depending on their addition amount. Accordingly, when parahydroxybenzoic acid ester is added to a product to be antisepticized, an antiseptic composition including alcohols such as ethanol as a solubilizer has been generally used.

However, even the antiseptic composition including a solubilizer may be precipitated as crystals during storage at a low temperature, and cannot contain parahydroxybenzoic acid ester at a high concentration. A single parahydroxybenzoic acid ester may not provide a sufficient antibacterial effect, and a plurality of parahydroxybenzoic acid esters are often used concurrently in order to compensate for the antibacterial effect. However, in such an antiseptic composition, precipitation of crystals during storage at a low temperature is remarkable, and resulted preparations are handled with difficulty.

In order to improve the solubility of parahydroxybenzoic acid ester as described above, a variety of investigations has been hitherto conducted.

JP-B-S37-17994 describes an anti-mold agent comprising, as a main component, a eutectic mixture or a eutectic of two or more paraoxybenzoic acid esters. In this anti-mold agent, a plurality of paraoxybenzoic acid esters are formed into a eutectic mixture or a eutectic so that the solubility in water is considerably improved; however, the eutectic mixture or the eutectic are easily recrystallized, and it is necessary to add an emulsifier or the like in order to stably supply preparations.

JP-A-H09-124414 describes a synergistic antimicrobial agent comprising 1,2-dibromo-2,4-dicyanobutane; and at least one parahydroxybenzoic acid ester. However, such an antimicrobial agent is high in price, and is insufficient in toxicity and safety data.

JP-A-2003-252799 describes a solubilizing aid of paraoxybenzoic acids comprising an aqueous solution containing a 2-methacryloyloxyethylphosphorylcholine/butyl methacrylate copolymer. However, it is necessary that 2-methacryloyloxyethylphosphorylcholine and butyl methacrylate are subjected to radical polymerization under an inert gas atmosphere in order to obtain the copolymer, and thus such a solubilizing aid is very troublesome in production thereof, and is high in price.

Accordingly, an antiseptic composition which is inexpensive, safe and excellent in antiseptic effect, and suppresses recrystallization of parahydroxybenzoic acid ester during storage at a low temperature has been desired.

SUMMARY OF THE INVENTION

An object of the present invention is to provide a liquid antiseptic composition which has improved stability during storage at a low temperature, and is excellent in antiseptic property.

The present inventors have intensively conducted investigations. As a result, the present inventors found that by mixing specified parahydroxybenzoic acid esters and specified organic solvents at specified ratio, precipitation of the parahydroxybenzoic acid ester during storage at a low temperature is prevented and, at the same time, an aqueous solution containing the parahydroxybenzoic acid ester at a high concentration is obtained. These findings have led to completion of the present invention.

That is, the present invention provides a liquid antiseptic composition comprising (A) parahydroxybenzoic acid ester, and (B) water-miscible organic solvent, wherein the (A) parahydroxybenzoic acid ester are two or more esters selected from the group consisting of methyl parahydroxybenzoate, ethyl parahydroxybenzoate, propyl parahydroxybenzoate, isopropyl parahydroxybenzoate, butyl parahydroxybenzoate, isobutyl parahydroxybenzoate and benzyl parahydroxybenzoate;

the (B) water-miscible organic solvent contains (B-1) at least one organic solvent selected from the group consisting of propylene glycol, butylene glycol, ethanol and polyethylene glycol, and (B-2) 2-phenoxyethanol; and a weight ratio of (A) and (B) is 1:1 to 1:3, and a weight ratio of (B-1) and (B-2) is 1:1 to 1:3.

The present invention also provides a production process of a liquid antiseptic composition, comprising a step of dissolving (A) parahydroxybenzoic acid ester in (B) water-miscible organic solvent at a temperature of 40 to 80° C., wherein the (A) parahydroxybenzoic acid ester are two or more esters selected from the group consisting of methyl parahydroxybenzoate, ethyl parahydroxybenzoate, propyl parahydroxybenzoate, isopropyl parahydroxybenzoate, butyl parahydroxybenzoate, isobutyl parahydroxybenzoate and benzyl parahydroxybenzoate;

the (B) water-miscible organic solvent contains (B-1) at least one organic solvent selected from the group consisting of propylene glycol, butylene glycol, ethanol and polyethylene glycol, and (B-2) 2-phenoxyethanol; and a weight ratio of (A) and (B) is 1:1 to 1:3, and a weight ratio of (B-1) and (B-2) is 1:1 to 1:3.

DETAILED DESCRIPTION OF THE INVENTION

Parahydroxybenzoic acid ester used in the liquid antiseptic composition of the present invention may be any combination, as far as the combination includes two or more esters selected from the group consisting of methyl parahydroxybenzoate, ethyl parahydroxybenzoate, propyl parahydroxybenzoate, isopropyl parahydroxybenzoate, butyl parahydroxybenzoate, isobutyl parahydroxybenzoate and benzyl parahydroxybenzoate. In one aspect, the parahydroxybenzoic acid ester are two or more esters, preferably two selected from the group consisting of methyl parahydroxybenzoate, ethyl parahydroxybenzoate, propyl parahydroxybenzoate and butyl parahydroxybenzoate. In view of solubility in water and an antiseptic effect, a combination of methyl parahydroxybenzoate and ethyl parahydroxybenzoate, a combination of propyl parahydroxybenzoate and butyl parahydroxybenzoate, and a combination of methyl parahydroxybenzoate and propyl parahydroxybenzoate are preferable.

A blending ratio of the parahydroxybenzoic acid ester may differ depending on the kinds and numbers of esters to be selected. For example, when methyl parahydroxybenzoate and ethyl parahydroxybenzoate are selected, the blending ratio of methyl parahydroxybenzoate and ethyl parahydroxybenzoate is preferably 3:1 to 1:3, more preferably 2:1 to 1:2, and further preferably 1:0.7 to 1:1.5.

When propyl parahydroxybenzoate and butyl parahydroxybenzoate are selected, a weight ratio of propyl parahydroxybenzoate and butyl parahydroxybenzoate is preferably 3:1 to 1:3, more preferably 2:1 to 1:2, and further preferably 1:0.7 to 1:1.5.

When methyl parahydroxybenzoate and propyl parahydroxybenzoate are selected, a weight ratio of methyl parahydroxybenzoate and propyl parahydroxybenzoate is preferably 3:1 to 1:3, more preferably 2:1 to 1:2, and further preferably 1:0.7 to 1:1.5.

A percentage of the parahydroxybenzoic acid ester in the liquid antiseptic composition of the present invention is not particularly limited as far as the amount of the ester does not cause precipitation during storage at a low temperature, but the total amount of the parahydroxybenzoic acid ester is preferably 25 to 50% by weight, more preferably 30 to 45% by weight, and further preferably 33 to 42% by weight based on the whole amount of the liquid antiseptic composition. When the total amount of the parahydroxybenzoic acid ester is less than 25% by weight based on the whole amount of the liquid antiseptic composition, the antiseptic effect tends to be insufficient, and when the total amount of the parahydroxybenzoic acid ester is more than 50% by weight based on the whole amount of the liquid antiseptic composition, precipitation tends to be easily caused during storage at a low temperature.

The water-miscible organic solvent used in the present invention is a mixed solvent including first and second organic solvents. The first organic solvent (B-1) is at least one organic solvent selected from the group consisting of propylene glycol, butylene glycol, ethanol and polyethylene glycol, and in view of solubility of the parahydroxybenzoic acid ester, propylene glycol (e.g., 1,2-propanediol or 1,3-propanediol) or butylene glycol (e.g., 1,3-butanediol or 1,4-butanediol) is preferable. The second organic solvent (B-2) is 2-phenoxyethanol.

A weight ratio of the organic solvent (B-1) and the organic solvent (B-2) in the water-miscible organic solvent should be 1:1 to 1:3. The weight ratio of the organic solvent (B-1) and the organic solvent (B-2) is preferably 1:1.5 to 1:2.5, and more preferably 1:1.8 to 1:2.2. When the weight of the organic solvent (B-2) relative to that of the organic solvent (B-1) is less than an equal amount, the parahydroxybenzoic acid ester tend to be precipitated at a low temperature, and when the weight of the organic solvent (B-2) is more than a 3-fold amount of the weight of the organic solvent (B-1), the solubility of the parahydroxybenzoic acid ester in water tends to be lower.

A percentage of the water-miscible organic solvent in the liquid antiseptic composition of the present invention is not particularly limited as far as the amount of the organic solvent is an amount at which the parahydroxybenzoic acid ester are soluble, but the total amount of the water-miscible organic solvent based on the whole amount of the liquid antiseptic composition is preferably 50 to 75% by weight, more preferably 55 to 70% by weight, and further preferably 58 to 67% by weight. When the total amount of the water-miscible organic solvent is less than 50% by weight based on the whole amount of the liquid antiseptic composition, precipitation of the parahydroxybenzoic acid ester tends to easily occur during storage at a low temperature. When the total amount of the water-miscible organic solvent is more than 75% by weight based on the whole amount of the liquid antiseptic composition, the antiseptic effect tends to be insufficient.

A weight ratio of the parahydroxybenzoic acid ester and the water-miscible organic solvent in the liquid antiseptic composition of the present invention should be 1:1 to 1:3, and is preferably 1:1.2 to 1:2, and more preferable 1:1.4 to 1:1.8. When the weight of the water-miscible organic solvent relative to that of the parahydroxybenzoic acid ester is less than an equal amount, precipitation of the parahydroxybenzoic acid ester tends to easily occur during storage at a low temperature. When the weight of the water-miscible organic solvent is more than a 3-fold amount of the weight of the parahydroxybenzoic acid ester, the antiseptic effect tends to be insufficient.

The liquid antiseptic composition of the present invention may be produced by mixing the parahydroxybenzoic acid ester and the water-miscible organic solvent at a weight ratio of 1:1 to 1:3, and dissolving the parahydroxybenzoic acid ester at a temperature of 40 to 80° C. The temperature at which the parahydroxybenzoic acid ester are dissolved is preferably 45 to 75° C., and more preferably 50 to 70° C.

The liquid antiseptic composition thus obtained may be used for a variety of subjects which need antiseptic treatment after cooling to room temperature. As a method for applying the liquid antiseptic composition to a subject to be antisepticized, the resulting liquid antiseptic composition may be directly applied to the subject, or if necessary, after the liquid antiseptic composition is formed into an aqueous solution, the solution may be then applied to the subject. Examples of the method for applying the liquid antiseptic composition to the subject include, but are not limited to, addition, mixing, coating, impregnation and the like.

Examples of the specific subject to be antisepticized include cosmetics, medicaments, foods, ink, metal processing oils, adhesives, water, paints, refrigerants, insect repellants, aromatic agents, deodorizing agents, non-woven fabrics and the like.

The liquid antiseptic composition is applied to the subject to be antisepticized such that a percentage of the parahydroxybenzoic acid ester based on the whole weight of the subject is preferably 0.01 to 5% by weight, more preferably 0.02 to 1% by weight, and further preferably 0.05 to 0.5% by weight.

The liquid antiseptic composition of the present invention may contain an accessory ingredient in such a range that the stability during storage at a low temperature and the antiseptic property are not affected. Examples of the accessory ingredient include pH adjusting agents, surfactants, stabilizers, viscosity adjusting agents, coloring agents, perfumes and the like. A percentage of the accessory ingredient is preferably 0.01 to 1% by weight based on the whole amount of the liquid antiseptic composition.

The present invention will be further illustrated below by way of Examples.

EXAMPLES

Examples 1 to 7 and Comparative Examples 1 to 20

Production of Liquid Antiseptic Composition

Parahydroxybenzoic acid ester (A) shown in Table 1 were added to water-miscible organic solvent (B) shown in the same table, which had been obtained by mixing solvents in advance, and the materials were dissolved while heating to about 60° C., to produce a liquid antiseptic composition.

TABLE 1

| | (% by weight) | Example 1 | Example 2 | Example 3 | Example 4 | Example 5 |
|---|---|---|---|---|---|---|
| parahydroxybenzoic acid ester (A) | methyl parahydroxybenzoate | 21 | — | 21 | 21 | — |
| | ethyl parahydroxybenzoate | 16 | — | — | 16 | — |
| | propyl parahydroxybenzoate | — | 20 | 16 | — | 20 |
| | butyl parahydroxybenzoate | — | 20 | — | — | 20 |
| water-miscible organic solvent (B) | 1,2-propanediol | 21 | 20 | 21 | — | — |
| | 1,3-butanediol | — | — | — | 21 | 20 |
| | 2-phenoxyethanol | 42 | 40 | 42 | 42 | 40 |

| | (% by weight) | Comparative Example 1 | Comparative Example 2 | Comparative Example 3 | Comparative Example 4 | Comparative Example 5 |
|---|---|---|---|---|---|---|
| parahydroxybenzoic acid ester (A) | methyl parahydroxybenzoate | 37 | 20 | 10 | 37 | 20 |
| | ethyl parahydroxybenzoate | — | — | — | — | — |
| | propyl parahydroxybenzoate | — | — | — | — | — |
| | butyl parahydroxybenzoate | — | — | — | — | — |
| water-miscible organic solvent (B) | 1,2-propanediol | 63 | 80 | 90 | — | — |
| | 1,3-butanediol | — | — | — | — | — |
| | 2-phenoxyethanol | — | — | — | 63 | 80 |

| | (% by weight) | Comparative Example 6 | Comparative Example 7 | Comparative Example 8 | Comparative Example 9 | Comparative Example 10 |
|---|---|---|---|---|---|---|
| parahydroxybenzoic acid ester (A) | methyl parahydroxybenzoate | 15 | — | — | — | — |
| | ethyl parahydroxybenzoate | — | — | — | — | — |
| | propyl parahydroxybenzoate | — | — | — | — | — |
| | butyl parahydroxybenzoate | — | 40 | 20 | 40 | 20 |
| water-miscible organic solvent (B) | 1,2-propanediol | — | 60 | 80 | — | — |
| | 1,3-butanediol | — | — | — | — | — |
| | 2-phenoxyethanol | 85 | — | — | 60 | 80 |

| | (% by weight) | Comparative Example 11 | Comparative Example 12 | Comparative Example 13 | Comparative Example 14 | Comparative Example 15 |
|---|---|---|---|---|---|---|
| parahydroxybenzoic acid ester (A) | methyl parahydroxybenzoate | 21 | 21 | — | — | 37 |
| | ethyl parahydroxybenzoate | 16 | 16 | — | — | — |
| | propyl parahydroxybenzoate | — | — | 20 | 20 | — |
| | butyl parahydroxybenzoate | — | — | 20 | 20 | — |
| water-miscible organic solvent (B) | 1,2-propanediol | 63 | — | 60 | — | 21 |
| | 1,3-butanediol | — | — | — | — | — |
| | 2-phenoxyethanol | — | 63 | — | 60 | 42 |

| | (% by weight) | Comparative Example 16 | Comparative Example 17 | Comparative Example 18 | Comparative Example 19 | Comparative Example 20 |
|---|---|---|---|---|---|---|
| parahydroxybenzoic acid ester (A) | methyl parahydroxybenzoate | 30 | 20 | — | — | 21 |
| | ethyl parahydroxybenzoate | — | — | — | — | 16 |
| | propyl parahydroxybenzoate | — | — | — | — | — |
| | butyl parahydroxybenzoate | — | — | 40 | 35 | — |
| water-miscible organic solvent (B) | 1,2-propanediol | 20 | 25 | 20 | 20 | 42 |
| | 1,3-butanediol | — | — | — | — | — |
| | 2-phenoxyethanol | 50 | 55 | 40 | 45 | 21 |

| | (% by weight) | Example 6 | Example 7 |
|---|---|---|---|
| parahydroxybenzoic acid ester (A) | methyl parahydroxybenzoate | — | — |
| | ethyl parahydroxybenzoate | — | — |
| | propyl parahydroxybenzoate | 20 | 20 |
| | butyl parahydroxybenzoate | 20 | 20 |
| water-miscible organic solvent (B) | 1,3-propanediol | 20 | — |
| | 1,4-butanediol | — | 20 |
| | 2-phenoxyethanol | 40 | 40 |

Stability Test

Five milliliters of each liquid antiseptic composition produced as described above was placed in a vial bottle having a volume of 50 mL, the bottle was capped tightly and stored in a refrigerator at 4° C., and then an appearance after passage for 7 days was observed.

The liquid antiseptic compositions of the present invention (Examples 1 to 7) did not show precipitation or the like, and were stable. The results are shown in Table 2.

TABLE 2

|  | Example 1 | Example 2 | Example 3 | Example 4 | Example 5 |
|---|---|---|---|---|---|
| stability | good (stable) | good (stable) | good (stable) | good (stable) | good (stable) |
|  | Comparative Example 1 | Comparative Example 2 | Comparative Example 3 | Comparative Example 4 | Comparative Example 5 |
| stability | poor (precipitation) | poor (precipitation) | good (stable) | poor (precipitation) | poor (precipitation) |
|  | Comparative Example 6 | Comparative Example 7 | Comparative Example 8 | Comparative Example 9 | Comparative Example 10 |
| stability | good (stable) | poor (precipitation) | good (stable) | poor (precipitation) | good (stable) |
|  | Comparative Example 11 | Comparative Example 12 | Comparative Example 13 | Comparative Example 14 | Comparative Example 15 |
| stability | poor (precipitation) | poor (precipitation) | poor (precipitation) | poor (precipitation) | poor (precipitation) |
|  | Comparative Example 16 | Comparative Example 17 | Comparative Example 18 | Comparative Example 19 | Comparative Example 20 |
| stability | poor (precipitation) | good (stable) | poor (precipitation) | good (stable) | poor (precipitation) |
|  | Example 6 | | | Example 7 | |
| stability | good (stable) | | | good (stable) | |

Antibacterial Activity Test 1

Regarding the respective compositions of Examples 1, 3 and 4 as well as Comparative Examples 3, 6 and 17, which contained methyl parahydroxybenzoate and were stable in the stability test without precipitation, a minimum inhibitory concentration (MIC) was measured in accordance with Standard Method of Japanese Society of Chemotherapy (broth microdilution method).

Each composition was diluted with sterilized water to prepare a drug solution having a composition concentration of 0.003 to 0.4% by weight, an SCD bouillon medium a concentration of which had been adjusted to a concentration of 2-fold of the designated concentration (manufactured by Nihon Pharmaceutical Co., Ltd.) was added at the same amount as that of the drug solution, and after stirring, each 170 μL/well was dispensed into a microtiter plate (96-well). Then, a bacterial liquid obtained by culturing each of the following test bacteria in an SCD medium at 30° C. for 20 hours was diluted with physiological saline so as to have a concentration of $10^4$ cfu/ml, and each 10 μL/well was inoculated on a microtiter plate produced as described above and to which the medium had been dispensed. This was cultured in an incubator at 30° C. for 48 hours, the presence or absence of growth of bacteria was confirmed visually, and the MIC was measured. The results are shown in Table 3.

Test bacterium 1: *Escherichia coli* NIHJ-JC2
Test bacterium 2: *Staphylococcus aureus* IF013276
Test bacterium 3: *Pseudomonas aeruginosa* ATCC13736
Test bacterium 4: *Candida albicans* FDA2138
Test bacterium 5: *Aspergillus niger* ATCC16404

TABLE 3

|  | Example 1 (ppm) | Example 3 (ppm) | Example 4 (ppm) |
|---|---|---|---|
| *Escherichia coli* | 1000 | 1000 | 1000 |
| *Staphylococcus aureus* | 2000 | 1000 | 2000 |
| *Pseudomonas aeruginosa* | 2000 | 1000 | 2000 |
| *Candida albicans* | 1000 | 500 | 1000 |
| *Aspergillus niger* | 500 | 250 | 500 |
|  | Comparative Example 3 (ppm) | Comparative Example 6 (ppm) | Comparative Example 17 (ppm) |
| *Escherichia coli* | 2000 | 2000 | 1000 |
| *Staphylococcus aureus* | 2000 | 2000 | 2000 |
| *Pseudomonas aeruginosa* | 4000 | 4000 | 2000 |
| *Candida albicans* | 2000 | 2000 | 1000 |
| *Aspergillus niger* | 2000 | 2000 | 1000 |

Antibacterial Activity Test 2

Regarding the respective compositions of Examples 2 and 5 to 7 as well as Comparative Examples 8, 10 and 19, which contained butyl parahydroxybenzoate and were stable in the stability test without precipitation, the MIC was measured using the same method and the same test bacterium as those of the antibacterial activity test 1. The results are shown in Table 4.

TABLE 4

|  | Example 2 (ppm) | Example 5 (ppm) | Example 6 (ppm) | Example 7 (ppm) |
|---|---|---|---|---|
| *Escherichia coli* | 500 | 500 | 500 | 500 |
| *Staphylococcus aureus* | 250 | 250 | 500 | 500 |
| *Pseudomonas aeruginosa* | 1000 | 1000 | 1000 | 1000 |
| *Candida albicans* | 250 | 250 | 500 | 500 |
| *Aspergillus niger* | 125 | 125 | 125 | 125 |
|  | Comparative Example 8 (ppm) | Comparative Example 10 (ppm) | Comparative Example 19 (ppm) | |
| *Escherichia coli* | 1000 | 1000 | 1000 | |
| *Staphylococcus aureus* | 500 | 500 | 250 | |

TABLE 4-continued

| | | | |
|---|---|---|---|
| Pseudomonas aeruginosa | 2000 | 2000 | 1000 |
| Candida albicans | 1000 | 1000 | 500 |
| Aspergillus niger | 500 | 500 | 250 |

Test of Solubility in Water

Regarding the respective compositions of Examples 1, 3 and 4 as well as Comparative Examples 3, 6 and 17, which contained methyl parahydroxybenzoate and were stable in the stability test without precipitation, 100 mL of an aqueous saturated solution (it was determined that saturation was reached at the time point at which the parahydroxybenzoic acid ester was precipitated), and the total amount of the parahydroxybenzoic acid esters in the aqueous solution was compared with one another. Separately, regarding the respective compositions of Examples 2 and 5 to 7 as well as Comparative Examples 8, 10 and 19, which contained butyl parahydroxybenzoate and were stable without precipitation, the comparison was also conducted in the same manner as described above.

The aqueous solutions including the liquid antiseptic composition of the present invention contained the parahydroxybenzoic acid ester at a higher concentration as compared with the aqueous solutions of Comparative Examples. The results are shown in Tables 5 and 6.

TABLE 5

| | Example 1 | Example 3 | Example 4 |
|---|---|---|---|
| total amount of parahydroxybenzoic acid ester (g/100 mL) | 0.26 | 0.20 | 0.26 |

| | Comparative Example 3 | Comparative Example 6 | Comparative Example 17 |
|---|---|---|---|
| total amount of parahydroxybenzoic acid ester (g/100 mL) | 0.12 | 0.15 | 0.12 |

TABLE 6

| | Example 2 | Example 5 | Example 6 | Example 7 |
|---|---|---|---|---|
| total amount of parahydroxybenzoic acid ester (g/100 mL) | 0.04 | 0.04 | 0.04 | 0.04 |

| | Comparative Example 8 | Comparative Example 10 | Comparative Example 19 |
|---|---|---|---|
| total amount of parahydroxybenzoic acid ester (g/100 mL) | 0.02 | 0.02 | 0.0175 |

What is claimed is:

1. A liquid antiseptic composition comprising
(A) parahydroxybenzoic acid esters, and
(B) water-miscible organic solvent,
wherein the (A) parahydroxybenzoic acid esters are two or more esters selected from the group consisting of methyl parahydroxybenzoate, ethyl parahydroxybenzoate, propyl parahydroxybenzoate, isopropyl parahydroxybenzoate, butyl parahydroxybenzoate, isobutyl parahydroxybenzoate and benzyl parahydroxybenzoate;
the (B) water-miscible organic solvent contains (B-1) at least one organic solvent selected from the group consisting of propylene glycol, butylene glycol, ethanol and polyethylene glycol, and (B-2) 2-phenoxyethanol; and
a weight ratio of (A) and (B) is 1:1 to 1:3, and a weight ratio of (B-1) and (B-2) is 1:1 to 1:3.

2. The liquid antiseptic composition according to claim 1, wherein a total amount of the (A) parahydroxybenzoic acid esters is 25 to 50% by weight based on the whole amount of the liquid antiseptic composition, and a total amount of the (B) water-miscible organic solvent is 50 to 75% by weight based on the whole amount of the liquid antiseptic composition.

3. The liquid antiseptic composition according to claim 1, wherein the (A) parahydroxybenzoic acid esters are methyl parahydroxybenzoate and ethyl parahydroxybenzoate.

4. The liquid antiseptic composition according to claim 3, wherein a weight ratio of methyl parahydroxybenzoate and ethyl parahydroxybenzoate is 3:1 to 1:3.

5. The liquid antiseptic composition according to claim 1, wherein the (A) parahydroxybenzoic acid esters are propyl parahydroxybenzoate and butyl parahydroxybenzoate.

6. The liquid antiseptic composition according to claim 5, wherein a weight ratio of propyl parahydroxybenzoate and butyl parahydroxybenzoate is 3:1 to 1:3.

7. The liquid antiseptic composition according to claim 1, wherein the (B-1) organic solvent is propylene glycol or butylene glycol.

8. The liquid antiseptic composition according to claim 1, wherein a subject to be antisepticized is any one selected from the group consisting of a cosmetic, a medicament, a food, ink, a metal processing oil, an adhesive, industrial water, a paint, a refrigerant, an insect repellant, an aromatic agent, a deodorizing agent and a non-woven fabric.

9. A production process of a liquid antiseptic composition, comprising a step of dissolving (A) parahydroxybenzoic acid esters in (B) a water-miscible organic solvent at a temperature of 40 to 80° C.,
wherein the (A) parahydroxybenzoic acid esters are two or more esters selected from the group consisting of methyl parahydroxybenzoate, ethyl parahydroxybenzoate, propyl parahydroxybenzoate, isopropyl parahydroxybenzoate, butyl parahydroxybenzoate, isobutyl parahydroxybenzoate and benzyl parahydroxybenzoate;
the (B) water-miscible organic solvent contains (B-1) at least one organic solvent selected from the group consisting of propylene glycol, butylene glycol, ethanol and polyethylene glycol, and (B-2) 2-phenoxyethanol; and
a weight ratio of (A) and (B) is 1:1 to 1:3, and a weight ratio of (B-1) and (B-2) is 1:1 to 1:3.

* * * * *